United States Patent
Liu et al.

(10) Patent No.: US 7,559,253 B2
(45) Date of Patent: Jul. 14, 2009

(54) METHOD FOR MEASURING BONDING FORCE BETWEEN SUBSTRATE AND CARBON NANOTUBE ARRAY FORMED THEREON

(75) Inventors: Kai Liu, Beijing (CN); Kai-Li Jiang, Beijing (CN); Shou-Shan Fan, Beijing (CN)

(73) Assignees: Tsinghua University, Beijing (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 43 days.

(21) Appl. No.: 11/848,186

(22) Filed: Aug. 30, 2007

(65) Prior Publication Data
US 2008/0173098 A1      Jul. 24, 2008

(30) Foreign Application Priority Data
Sep. 1, 2006   (CN) .......................... 2006 1 0062428

(51) Int. Cl.
*G01N 3/08*   (2006.01)
(52) U.S. Cl. .......................................... 73/827; 73/842
(58) Field of Classification Search .................. 73/827, 73/842
See application file for complete search history.

(56) References Cited

U.S. PATENT DOCUMENTS

2002/0194930 A1* 12/2002 Crosby et al. ................. 73/827
2004/0142172 A1*  7/2004 Sugiyama et al. ............ 428/403
2007/0228591 A1* 10/2007 Rey ............................ 264/40.1
2008/0202254 A1*  8/2008 Deng et al. .................... 73/827
2009/0011232 A1*  1/2009 Dai et al. ................. 428/355 R
2009/0047513 A1*  2/2009 Lashmore .................... 428/340

OTHER PUBLICATIONS

Yang et al. Toward the Chemistry of Carboxylic Single-Walled Carbon Nanotubes by Chemical Force Microscopy. Journal of Physical Chemistry. 2002.*
Bottomley et al. Force Spctroscopy of Single Walled Carbon Nanotubes for Improved Polymer Composites. American Chemical Society. 2004.*
Bottomley et al. Fly-Fishing with Single Walled Carbon Nanotubes. Abstract of Papers, 227th ACS National Meeting. 2004.*

* cited by examiner

*Primary Examiner*—Lisa M Caputo
*Assistant Examiner*—Freddie Kirkland, III
(74) *Attorney, Agent, or Firm*—D. Austin Bonderer

(57) ABSTRACT

A method for measuring a bonding force between a substrate (50) and a carbon nanotube array (40) formed thereon, wherein the carbon nanotube array includes a plurality of carbon nanotubes. A force gauge (1) including a cantilever (10), a flat-surface probe (20), a movement mechanism (60), and a force sensor (70) is provided. The probe is secured at one end of the cantilever. An adhesive layer (30) is formed on the flat surface of the probe. The probe is moved toward the substrate and is brought into bonding contact with the carbon nanotube array by the movement mechanism. The probe is pulled away from the substrate by the movement mechanism, causing the carbon nanotubes adhered thereto to separate from the substrate. The force at separation is detected by the force sensor, and that force can be converted into an average nanotube/substrate bonding force/strength.

15 Claims, 3 Drawing Sheets

METHOD FOR MEASURING BONDING FORCE BETWEEN SUBSTRATE AND CARBON NANOTUBE ARRAY FORMED THEREON

BACKGROUND OF THE INVENTION

1. Field of the Invention

The invention relates to a method for measuring a bonding force and, particularly, to a method for measuring a bonding force between a substrate and a carbon nanotube array formed thereon.

2. Description of Related Art

Carbon nanotubes (CNTs) are a carbonaceous material discovered by Iijima, a researcher of NEC Corporation, in 1991. Carbon nanotubes are electrically conductive along their length, are chemically stable, and can each have a very small diameter (much less than 100 nanometers) and a large aspect ratio (i.e., the ratio of length to diameter). Due to these and other properties, it has been suggested that carbon nanotubes can play an important role in fields such as microscopic electronics, field emission devices, thermal interface materials, etc.

Generally, a CNT field emission display device includes a substrate and a carbon nanotube array formed on the substrate. The carbon nanotube array acts as an electron emitter for emitting electrons, which collide with a phosphor layer disposed opposite to the carbon nanotube array, thereby stimulating light emission upon such collision. A bonding force or strength between the carbon nanotube array and the substrate is considered an important factor related to the performance of the CNT field emission display. Undesirable phenomena, such as short circuits, electrical discharges, or complete electrical disconnects, may occur if the bonding force between the carbon nanotube array and the substrate is weak. Therefore, it is important to determine whether the bonding force between the carbon nanotube array and the substrate is strong enough to guarantee good performance of the CNT field emission display, especially over a suitable lifetime for such. Thus, a method for effectively measuring the bonding force between the substrate and the carbon nanotube array is needed.

The conventional methods employed to measure the bonding force usually use an atomic force microscope (AFM) or an mN force gauge. The AFMs suffer from the limitation that they can merely measure a single carbon nanotube or a few carbon nanotubes at a time. Therefore, it can be seen that it is impractical to use AFMs to measure the carbon nanotubes in mass production. In addition, a Van der Waals force between each carbon nanotubes will interfere with the measuring results, so that the precision of measuring results is decreased accordingly. For example, added Van der Waals force between proximate carbon nanotubes can create the appearance of a larger carbon nanotube to substrate bonding force than what actually exists.

However, the mN force gauge will generate noise during measurement, due much in part to the aforementioned Van der Waals force that exists between adjoining carbon nanotubes. A signal-to-noise ratio of measurement is relative low, thus making it difficult to make accurate and/or precise measurements.

What is needed, therefore, is a method for measuring a bonding force between a substrate and a carbon nanotube array formed thereon that has improved efficiency and provides more precise measuring results of such bonding force.

SUMMARY OF THE INVENTION

A method for measuring a bonding force/strength between a substrate and a carbon nanotube array formed thereon is provided. The carbon nanotube array includes a plurality of carbon nanotubes. In one present embodiment, the method includes the steps described as follows. A force gauge, including a cantilever, a probe, a movement mechanism and a force sensor, is provided. The probe is secured at one end of the cantilever and has a flat surface. An adhesive layer is formed on the flat surface of the probe. The probe is moved toward the substrate and is brought into a close proximity of the carbon nanotube array by the movement mechanism to cause the adhesive layer on the flat surface to contact the carbon nanotubes and thereby adhere to the probe. The probe is pulled directionally away from the substrate by the movement mechanism, causing the carbon nanotubes adhered thereto to separate from the substrate. A value of the bonding force/strength between the carbon nanotube array and the substrate is obtained by calculating a relationship between a number of the carbon nanotubes adhered to the adhesive layer and a force value detected by the force sensor.

Other advantages and novel features of the present method for measuring a bonding force between a substrate and a carbon nanotube array formed thereon will become more apparent from the following detailed description of at least one preferred embodiment, when taken in conjunction with the accompanying drawings.

BRIEF DESCRIPTION OF THE DRAWINGS

Many aspects of the present method for measuring a bonding force/strength between a substrate and a carbon nanotube array formed thereon can be better understood with reference to the following drawings. The components in the drawings are not necessarily to scale, the emphasis instead being placed upon clearly illustrating the principles of the present method for measuring a bonding force/strength between a substrate and a carbon nanotube array formed thereon.

Figure 1:
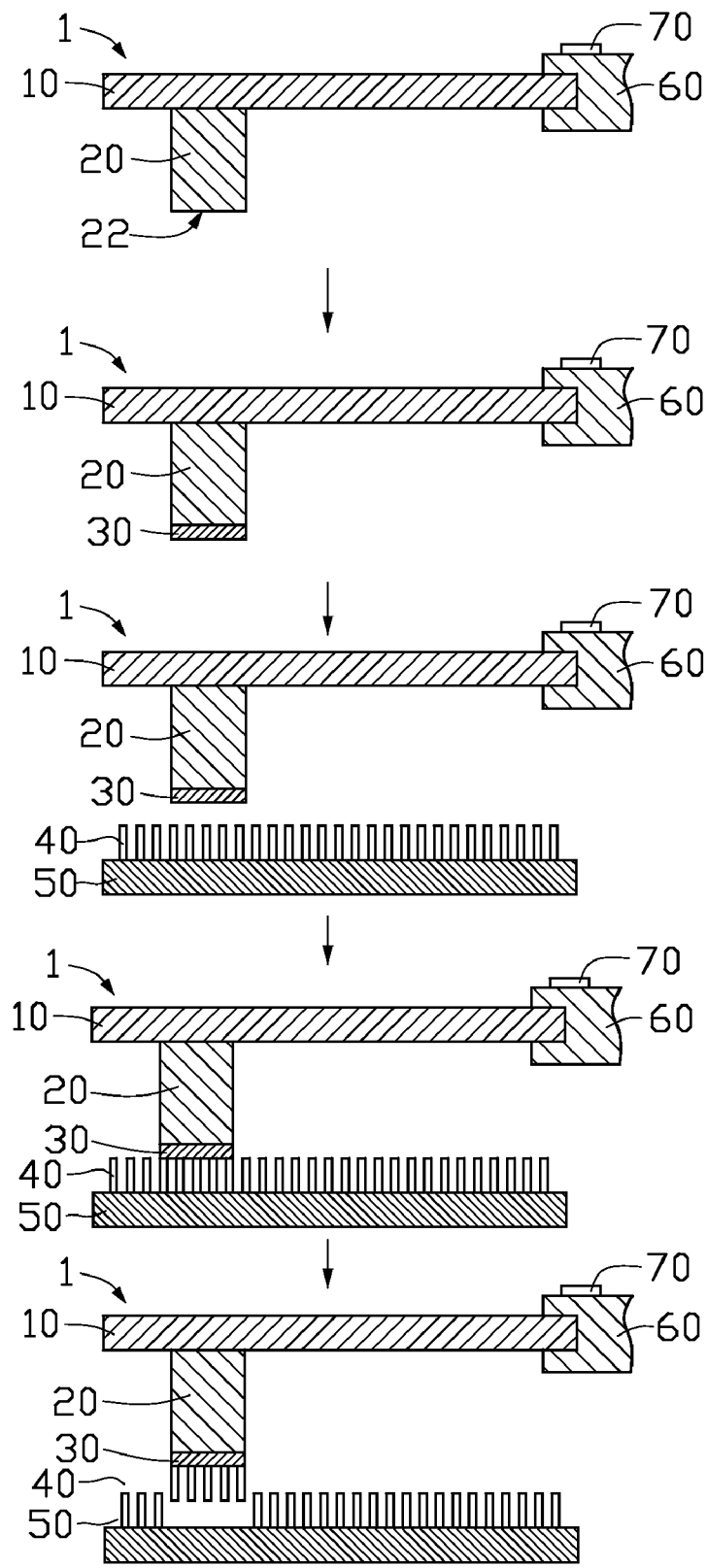
FIG. 1 is a flowchart of a method for measuring a bonding force between a substrate and a carbon nanotube array formed thereon, in accordance with a present embodiment.

Corresponding reference characters indicate corresponding parts throughout the several views. The exemplifications set out herein illustrate at least one preferred embodiment of the present method for measuring a bonding force between a substrate and a carbon nanotube array formed thereon, in one form, and such exemplifications are not to be construed as limiting the scope of the invention in any manner.

DETAILED DESCRIPTION OF THE INVENTION

Reference will now be made to the drawings to describe at least one embodiment of the present method for measuring a bonding force/strength between a substrate and a carbon nanotube array formed thereon, in detail.

Referring to FIG. 1, a method for measuring a bonding force between a substrate 50 and a carbon nanotube array 40 formed thereon, wherein the carbon nanotube array 40 includes a plurality of carbon nanotubes, according to a present embodiment, the method includes the following steps:

(a): providing a force gauge 1 including a cantilever 10, a probe 20, a movement mechanism 60, and a force sensor 70, wherein the probe 20 is secured at one end of the cantilever 10 and has a flat surface 22;

(b): forming an adhesive layer 30 on the flat surface 22 of the probe 20;

(c): bringing the probe 20 toward the substrate 50 and, ultimately, into close proximity with the carbon nanotube array 40 by the movement mechanism 60 in order to cause the adhesive layer 30 on the flat surface 22 to contact and bond with at least a portion of the carbon nanotubes;

(d): moving/pulling the probe 20 directionally (beneficially, perpendicularly) away from the substrate 50 by the movement mechanism 60, causing the carbon nanotubes bonded to the adhesive layer 30 to separate from the substrate 50; and (e): obtaining a value of the bonding force/strength between the carbon nanotube array 40 and the substrate 50 by calculating a relationship between a number of the carbon nanotubes adhered to the adhesive layer 30 and a force value detected by the force sensor 70.

Each step of the present method is described in greater detail below.

Step (a) provides the force gauge 1, which has the cantilever 10, the probe 20, the movement mechanism 60, and a force sensor 70. An end of the probe 20 is fixed at the end of the cantilever 10. An opposite end of the probe 20 has a flat surface 22, whose area is, advantageously, relatively larger than that of conventional probe of the force gauge. In the present embodiment, the flat surface 22 is configured for facilitating measurement of the bonding force of a plurality of carbon nanotubes, relative to a substrate 50, by providing a means of connecting the cantilever 10 to a specimen to be tested (e.g., a group of bonded carbon nanotubes).

In the present embodiment, the probe 20 is adhered to the end of the cantilever 10. For example, the probe 20 can be adhered to the end of the cantilever 10 by an adhesive gel. However, the method for securing the probe 20 to the cantilever 10 is not limited to what is mentioned above, other methods/means (e.g., other bonding agents) known by persons having ordinary skill in the art also can be employed to achieve the desired attachment.

The probe 20 of the force gauge 1 can, for example, be filament-shaped. An end surface of the probe 20, which forms the flat surface 22, is, usefully, polished (i.e., mechanically and/or chemically) to be flat and smooth. In order to ensure a relatively large area for the flat surface 22, a diameter of a cross-section of the probe 20 is larger than or equal to about 200 μm. Beneficially, the filament-shaped probe 20 is a tungsten filament whose diameter is about 500 μm.

Alternatively, the probe 20 of the force gauge 1 can be strip-shaped. An end surface of the probe 20 used for facilitating the measuring of the bonding force usefully is flat, in order to simplify the calculation involved (i.e., no force angles/vectors to consider). In addition, in order to make sure that an area of the flat surface 22 of the strip-shaped probe 20 is large enough to measure the bonding force, the area should advantageously be greater than or equal to an approximate area of 150 μm×150 μm. In such case, the strip-shaped probe 20 is beneficially a silicon strip.

In step (b), the adhesive layer 30 is formed on the flat surface 22 of the probe 20. In particular, the adhesive layer 30 is formed by coating the flat surface 22.

In step (c), using the movement mechanism 60 of the force gauge 1, the probe 20 is brought toward the carbon nanotube array 40 and the substrate 50 until the adhesive layer 30 on the flat surface 22 contacts a plurality of the carbon nanotubes (e.g., the number of carbon nanotubes directly adjacent the flat surface 22 of the probe 20). As a result, the plurality of carbon nanotubes is adhered to the adhesive layer 30. In step (d), the probe 20 is moved/pulled away from the substrate 50 using the movement mechanism 60. In the pulling process, at least a portion of the plurality of the adhered carbon nanotubes separate from (i.e., become unbonded with) the substrate 50, as the adhesion force between carbon nanotubes and the adhesive layer 30 exceeds the average bonding force/strength between a given carbon nanotube and the substrate 50. Advantageously, the pulling direction is essentially perpendicular to the substrate 50, so that force vectors need not be considered in the calculation and so that basically only tension (i.e., little or no shear) force is involved in causing the carbon nanotubes to separate from the substrate 50.

In step (e), the value of the bonding force between the carbon nanotube array 40 and the substrate 50 can be finally obtained by calculating a relationship between the number of the carbon nanotubes adhered to the adhesive layer 30 and the force value displayed on the force gauge 1. The force sensor 70 is able to detect and transmit/output a signal (e.g., if digital) or a dial/gauge result (e.g., if mechanical), corresponding to the force applied during the process of pulling upon the plurality of the carbon nanotubes. That is, the force sensor 70 is configured for outputting a force readout associated with the pulling action. The maximum force detected by the force sensor 70 corresponds to the bonding force/strength for the group of carbon nanotubes removed during the test. In this case, the force value can be directly read out/from on the force gauge 1 and, particularly, the force sensor 70. The number of carbon nanotubes as well as an area of carbon nanotube distributed can be obtained using, e.g., a microscope. Advantageously, a scanning electron microscope (SEM) is used for this procedure, as use of an SEM would likely facilitate an automatic counting of the removed carbon nanotubes. Therefore, the bonding force of the carbon nanotubes and the substrate 50 per unit can be directly obtained by calculating the obtained values described above. As a result, the bonding force of the carbon nanotube array 40 and the substrate 50 can be calculated accordingly. Further, it is to be understood that, upon knowing the bonding area associated with that group of carbon nanotubes (i.e., number of nanotubes multiplied by the average cross-sectional area thereof), it would also be possible to convert the total measured bonding force/strength to an average maximum/bonding tensile stress (bonding force/unit area) for the carbon nanotubes.

Figure 2:
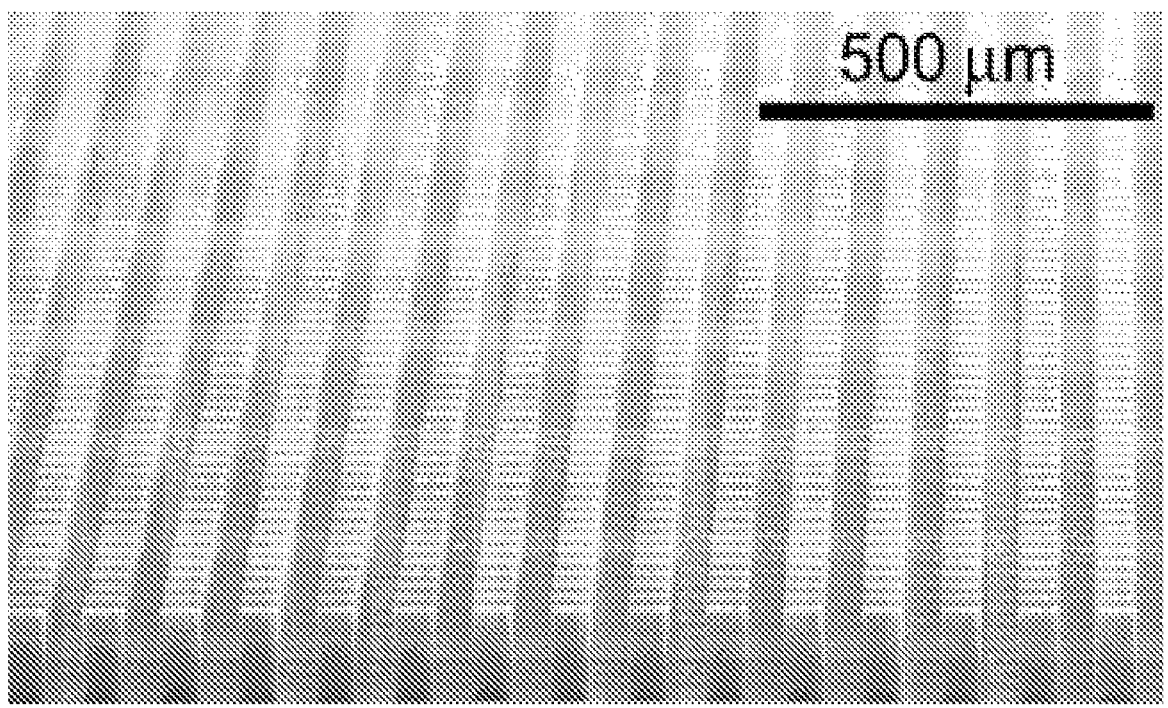
FIG. 2 is a view of a carbon nanotube array to be measured using the method illustrated in FIG. 1.
Figure 3:
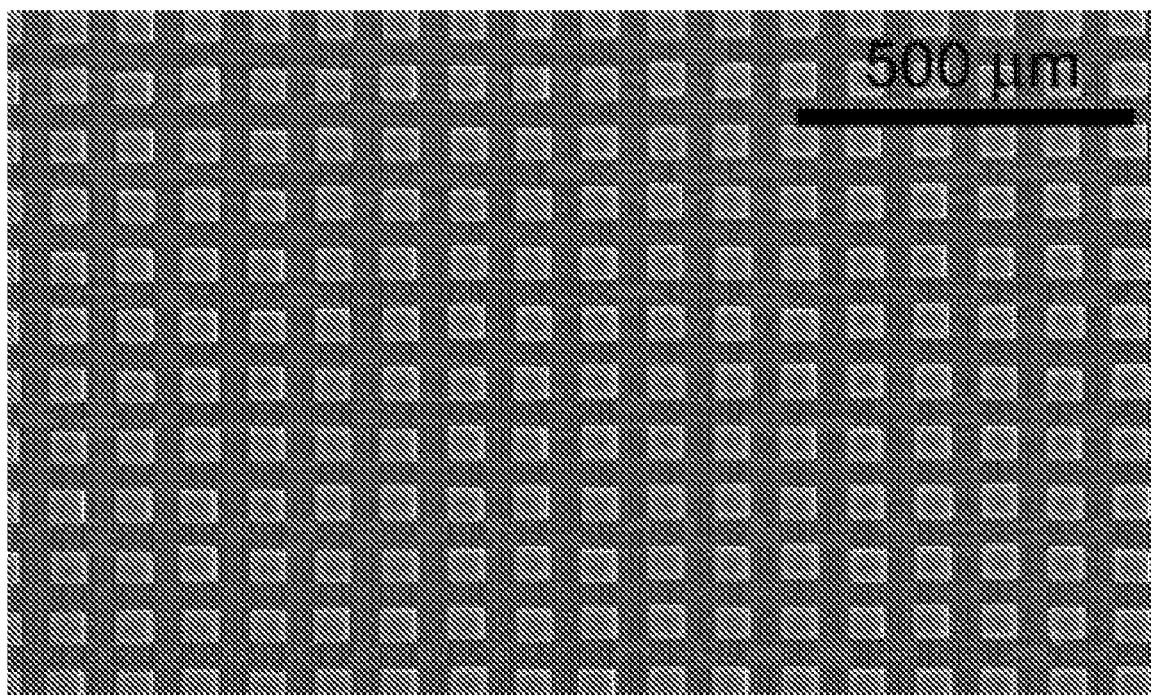
FIG. 3 is a vertical view of the carbon nanotube array of FIG. 2.

Referring to FIG. 2 and FIG. 3, the carbon nanotube array 40 includes a plurality of patterned units. Each of the patterned units includes a plurality of the carbon nanotubes. The patterned units have a distance therebetween, as shown in FIG. 3. In particular, the distance between the patterned units is kept uniformly constant over a large area. That is, the patterned units are arranged uniformly. Therefore, because some space is kept between the patterned units, the measuring results will not be influenced by Van der Waals force between such units. The precision of the measuring results can, therefore, be improved.

Each of the patterned units can, e.g., be a rectangle or square unit. In addition, an area of a cross-section of the patterned unit can correspond to an area of the flat surface 22 of the probe 20. For example, if an area of the flat surface 22 of the probe 20 is about 250 µm×250 µm or a diameter of the probe 20 is about 300 µm, an area of a cross-section of the patterned unit can be about 50 µm×50 µm.

Additionally, the carbon nanotube array 40 can be formed by a conventional method, such as chemical vapor deposition, arc discharging, or laser ablation. Usefully, the carbon nanotube array 40 is formed by chemical vapor deposition. More particularly, at first, a catalyst layer is formed on the substrate 50. The catalyst layer has a pattern corresponding to a pattern of the carbon nanotube array 40 to be formed. Finally, a carbon source gas is introduced at a higher treatment temperature to form the carbon nanotube array 40. In this case, the catalyst layer includes a catalyst material, which beneficially can be a transition metal selected from the group consisting of iron (Fe), cobalt (Co), nickel (Ni), palladium (Pd), and an alloy thereof. The carbon source gas can, advantageously, be methane, acetylene, ethylene, propylene, methanol, or ethanol.

In conclusion, the method for measuring the substrate and the carbon nanotube array formed thereon utilizes a probe, secured at one end of a cantilever, as part of a force gauge for measuring the bonding force. The probe has a flat surface whose area is large enough to sample several of the carbon nanotubes at a time. Therefore, the signal-to-noise ratio is raised during measurement. In addition, the carbon nanotube array to be evaluated includes a distance between the patterned units of the array. The distance can prevent or at least minimize the Van der Waals force from influencing the measuring results. As a result of such parameters involved with the present method, the precision of measuring results can be improved.

Finally, it is to be understood that the above-described embodiments are intended to illustrate rather than limit the invention. Variations may be made to the embodiments without departing from the spirit of the invention as claimed. The above-described embodiments illustrate the scope of the invention but do not restrict the scope of the invention.

What is claimed is:

1. A method for measuring a bonding force between a substrate and a carbon nanotube array grown thereon, the method comprising the following steps:

providing the substrate and the carbon nanotube array grown thereon, the carbon nanotube array comprising a plurality of carbon nanotubes, providing a force gauge including a cantilever, a probe, a movement mechanism and a force sensor, the probe being secured at one end of the cantilever and having a flat surface;

forming an adhesive layer on the flat surface of the probe;

bringing the probe the substrate and into proximity of the carbon nanotube array by the movement mechanism, causing the adhesive layer on the flat surface to contact the carbon nanotubes and thereby adhere to the probe;

pulling the probe away from the substrate by the movement mechanism, causing the carbon nanotubes adhered to the probe to separate from the substrate; and obtaining a value of the bonding force between the carbon nanotube array and the substrate by calculating a relationship between a number of the carbon nanotubes adhered to the adhesive layer and a force value detected by the force sensor.

2. The method as claimed in claim 1, wherein the probe is filament-shaped, and an end surface of the probe is polished to be the flat surface.

3. The method as claimed in claim 1, wherein a diameter of a cross-section of the probe is larger than or equal to about 200 µm.

4. The method as claimed in claim 1, wherein the probe is a tungsten filament, and a diameter of the tungsten filament is about 500 µm.

5. The method as claimed in claim 1, wherein the probe is strip-shaped, and an area of the flat surface is greater than or equal to an approximate area of 150 µm ×150 µm.

6. The method as claimed in claim 5, wherein the probe is a silicon strip.

7. The method as claimed in claim 1, wherein the probe is secured at the end of the cantilever by an adhesive gel.

8. The method as claimed in claim 1, wherein the carbon nanotube array comprises a plurality of patterned units having a distance therebetween.

9. The method as claimed in claim 8, wherein the patterned units are arranged uniformly 10. The method as claimed in claim 8, wherein the patterned unit is a rectangular unit, and an area of a cross-section of the rectangle unit is about 50 µm ×50 µm.

11. The method as claimed in claim 1, wherein the probe is pulled in a direction essentially perpendicular to the substrate.

12. The method as claimed in claim 1, wherein the carbon nanotubes in the carbon nanotube array are perpendicular to the substrate.

13. The method as claimed in claim 1, wherein the carbon nanotube array is grown on the substrate by chemical vapor deposition.

14. The method as claimed in claim 1, wherein the carbon nanotube array is grown by the following steps of: forming a catalyst layer on the substrate, the catalyst layer have a pattern corresponding to a pattern of the carbon nanotube array to be grown; and introducing a carbon source gas at a higher treatment temperature to grow the carbon nanotube array.

15. The method as claimed in claim 1, wherein the carbon nanotubes are adhered to the probe by the adhesive layer.

* * * * *